United States Patent
Harris et al.

[11] Patent Number: 5,922,922
[45] Date of Patent: *Jul. 13, 1999

[54] PROCESS FOR PRODUCING AN ALKYLATED, NON-OXYGEN-CONTAINING AROMATIC HYDROCARBON

[75] Inventors: Thomas V. Harris, Benicia; Curt B. Campbell, Hercules; Mohammed M. Habib, Benicia, all of Calif.

[73] Assignee: Chevron Chemical Company, San Ramon, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/895,540

[22] Filed: Jul. 17, 1997

Related U.S. Application Data

[63] Continuation of application No. 08/645,972, May 14, 1996, abandoned.

[51] Int. Cl.⁶ ............... C07C 2/68; C07C 2/64; C07C 5/22
[52] U.S. Cl. .......... 585/323; 585/467; 585/468; 585/671; 585/455
[58] Field of Search ................. 585/323, 467, 585/468, 671, 455

[56] References Cited

U.S. PATENT DOCUMENTS

| | | | |
|---|---|---|---|
| 2,404,340 | 7/1946 | Zimmerman | 260/671 |
| 3,288,716 | 11/1966 | Becraft et al. | 252/59 |
| 3,764,533 | 10/1973 | Hunt et al. | 252/33 |
| 4,108,889 | 8/1978 | Connor | 260/502.4 R |
| 4,259,193 | 3/1981 | Tirtiaux et al. | 252/33 |
| 4,324,940 | 4/1982 | Dessau | 585/466 |
| 4,503,277 | 3/1985 | Himes | 585/455 |
| 5,112,506 | 5/1992 | Marsh et al. | 252/33.4 |
| 5,177,280 | 1/1993 | Juguin et al. | 585/323 |
| 5,334,793 | 8/1994 | Kocal | 585/323 |

FOREIGN PATENT DOCUMENTS

| | | | |
|---|---|---|---|
| 0 001 318 | 12/1981 | European Pat. Off. | C07C 143/34 |
| 2 381 026 | 9/1978 | France | C07C 143/00 |
| 91/11411 | 8/1991 | WIPO | C07C 2/12 |
| 91/15443 | 10/1991 | WIPO | C07C 2/68 |
| 93/13038 | 7/1993 | WIPO | C07C 5/25 |

*Primary Examiner*—Hien Tran
*Assistant Examiner*—Thuan D. Dang
*Attorney, Agent, or Firm*—Ernest A. Schaal

[57] ABSTRACT

An alkylated aromatic hydrocarbon is produced having the following properties: (a) less than 40 wt. % of the alkylated aromatic hydrocarbon is 2-aryl; and (b) at least 20 wt. % of the alkylated aromatic hydrocarbon is a monoalkylate. That alkylated aromatic hydrocarbon is produced by isomerizing a normal alpha-olefin having from 20 to 28 carbon atoms in the presence of a first acidic catalyst to produce a partially-branched, isomerized olefin, then either benzene or toluene is alkylated with the partially-branched, isomerized olefin in the presence of a second solid, acidic catalyst. The first acidic catalyst can be a molecular sieve with a one-dimensional pore system. The second acidic catalyst can be a zeolite Y having a silica to alumina ratio of at least 40:1.

10 Claims, No Drawings

PROCESS FOR PRODUCING AN ALKYLATED, NON-OXYGEN-CONTAINING AROMATIC HYDROCARBON

This is a continuation of application Ser. No. 08/645,972 now abandoned, filed May 14, 1996.

The present invention relates to a catalyst system and process for alkylation of non-oxygen-maintaining aromatic hydrocarbons, such as benzene, toluene, xylene, cumene, or mixtures thereof, to provide an alkyl aromatic product, or alkylate, in which several chemical properties of the alkylate can be controlled.

BACKGROUND OF THE INVENTION

It is well known to catalyze the alkylation of aromatics with a variety of Lewis or Brönsted acid catalysts. Typical commercial catalysts include phosphoric acid/kieselguhr, aluminum halides, boron trifluoride, antimony chloride, stannic chloride, zinc chloride, onium poly(hydrogen fluoride), and hydrogen fluoride. Alkylation with lower molecular weight olefins, such as propylene, can be carried out in the liquid or vapor phase. For alkylations with higher olefins, such as $C_{16+}$ olefins, the alkylations are done in the liquid phase, usually in the presence of hydrogen fluoride. Alkylation of benzene with higher olefins is especially difficult, and requires hydrogen fluoride treatment. Such a process is disclosed by Himes in U.S. Pat. No. 4,503,277, entitled "HF Regeneration in Aromatic Hydrocarbon Alkylation Process," which is hereby incorporated by reference for all purposes. However, hydrogen fluoride is not environmentally attractive.

The use of these acids is extremely corrosive, thus requiring special handling and equipment. Also, the use of these acids might involve environmental problems. Another problem is that the use of these acids gives less than desirable control on the precise chemical composition of the product produced. Thus, it would be preferable to use a safer, simpler catalyst, preferably in solid state. This simpler process would result in less capital investment, which would result in a less expensive product.

The alkylates (alkyl aromatic hydrocarbons) typically produced by the catalytic alkylation of aromatics with Normal Alpha Olefins (NAO's) can be characterized by the following three chemical aspects of the alkylate:

1) the "2-aryl" content,
2) the "heavy alkylate" content, and
3) the "branching" content.

The "2-aryl content" is defined as the percentage of total mono-alkylate (the alkylate species in which one alkyl chain is attached to the aromatic ring) that is comprised of those chemical species in which the attachment of the alkyl chain to the aromatic ring is at the 2-position along the alkyl chain.

The "heavy alkylate" is defined as the percentage of the total alkylate that is comprised of those chemical species present with molecular weights higher than that of the mono-alkylate. These chemical species with molecular weights higher than that of the "mono-alkylate" may be composed of, but are not limited, to:

(a) mono-alkylate of oligomerized olefins,
(b) di-alkylated species, and
(c) oligomerized olefin species.

The "branching content" is defined as the percentage of the total mono-alkylate that is composed of chemical species in which the alkyl chain attached to the aromatic ring is not a simple straight chain or normal alkyl group, but those in which alkyl groups (such as methyl, ethyl, propyl, isopropyl, butyl, tert-butyl, isobutyl, and the various hexyl, heptyl and octyl isomers) are attached somewhere along the otherwise normal alkyl chain.

These three parameters are known to impart different properties to the corresponding sulfonates: Neutral, Low Overbased (LOB), or High Overbased (HOB). Thus, a process that allows one to control these three parameters simultaneously in a single process is tremendously advantageous from an efficiency standpoint in the production of alkylates.

For example, the "2-aryl" content is known to influence the performance of the corresponding sulfonate prepared from the alkylate in the area of laundry detergents [B. V. Vora, P. R. Pujado, T. Imai, T. R. Fritsch, paper presented in "Recent Advances in the Detergent Industry," *Society of Chemical Industry*, University of Cambridge, England, Mar. 26–28 (1990)]. Most solid acids produce high 2-aryl attachment when alkylating α-olefins. [See S. Sivasanker, A. Thangaraj, "Distribution of Isomers in the Alkylation of Benzene with Long-Chain Olefins over Solid Acid Catalysts," *Journal of Catalysis*, 138, 368–390 (1992)]. This is especially true for zeolite Y.

The "heavy alkylate" content is known to influence neutral sulfonates (U.S. Pat. Nos. 3,764,533 and 4,259,193) and overbased sulfonates and both neutral and HOB sulfonates (U.S. Pat. No. 5,112,506). Also, for applications where it is desired to have an alkylate with high "heavy content," being able to control the "heavy content" during the alkylation step has advantages over distilling the alkylate to obtain the desired molecular weight (U.S. Pat. No. 3,288,716). In U.S. Pat. No. 5,112,506, the effect of molecular weight distribution or "heavy alkylate" is shown to influence the performance of both neutral and HOB sulfonates and the dialkylate content is shown to influence the rust performance of the corresponding sulfonate in U.S. Pat. No. 3,764,533. In U.S. Pat. No. 4,259,193, a monoalkylate sulfonate is preferred. U.S. Pat. Nos. 3,288,716; 3,764,533; 4,259,193; and 5,112,506 are hereby incorporated by reference for all purposes.

The "branching" content is known to influence the performance of some sulfonates. In French Patent 2,381, 026 and European Patent 0,001,318, the linear olefin content, relative the branched olefin content, is shown to affect the foaming properties of a sulfonate. In these patents, they obtained the mixtures of the branched and linear alkylates by making physical blends of the two.

SUMMARY OF THE INVENTION

The present invention provides a process for producing an alkylated, non-oxygen-containing aromatic hydrocarbon where less than 40 wt. % of the alkylated aromatic hydrocarbon is 2-aryl, and at least 20 wt. %, preferably at least 75 wt. %, of the alkylated aromatic hydrocarbon is a monoalkylate.

That process involves isomerizing a normal alpha-olefin in the presence of a first acidic catalyst to produce a partially-branched, isomerized olefin, then alkylating a non-oxygen-containing aromatic hydrocarbon with the partially-branched, isomerized olefin in the presence of a second acidic catalyst.

Preferably, the normal alpha-olefin has from 14 to 30 carbon atoms. More preferably, it has from 20 to 28 carbon atoms.

Preferably, the non-oxygen-containing aromatic hydrocarbon is benzene, toluene, xylene, cumene, or mixtures thereof. More preferably, it is benzene or toluene.

Preferably, the first acidic catalyst is a solid catalyst having at least one metal oxide, which has an average pore size of less than 5.5 angstroms. More preferably, that solid catalyst is a molecular sieve with a one-dimensional pore system.

The second acidic catalyst is a solid catalyst that has at least one metal oxide and is a natural zeolite, a synthetic zeolite, a synthetic molecular sieve, or a clay. Preferably, it is an acidic molecular sieve or a zeolite, where the acidic molecular sieve or zeolite has an average pore size of at least 6.0 angstroms. More preferably, it is zeolite Y having a silica to alumina ratio of at least 40:1.

As used herein, the average pore size of a catalyst refers only to the pores within the active portion thereof, and does not include pores of any inactive binder or support used therewith.

As uses herein, all percentages are weight percent, unless otherwise specified.

DETAILED DESCRIPTION OF THE INVENTION

In its broadest aspect, the present invention involves a process for producing an alkylated, non-oxygen-containing aromatic hydrocarbon. That process comprises isomerizing a normal alpha-olefin in the presence of a first acidic catalyst to produce an isomerized olefin, then alkylating a non-oxygen-containing aromatic hydrocarbon with the isomerized olefin in the presence of a second, solid, acidic catalyst.

NON-OXYGEN-CONTAINING AROMATIC HYDROCARBONS

The non-oxygen-containing aromatic hydrocarbon that is alkylated in the subject process is preferably benzene or toluene, but a higher molecular eight hydrocarbon may also be charged to the process. Benzene is less reactive than substituted aromatics, therefore it requires higher temperatures to get high conversion. The feed aromatic hydrocarbon may, therefore, be toluene, xylene, ethylbenzene, naphthalene, etc., as long as it does not contain oxygen.

Preferably, the non-oxygen-containing aromatic hydrocarbon is benzene, toluene, xylene, cumene, or mixtures thereof. More preferably, it is benzene or toluene, because the resulting alkylates are more easily processed into the corresponding sulfonic acids or LOB and HOB sulfonates.

OLEFINS

The feed olefinic hydrocarbons that are consumed in the process are normal alpha-olefins that may have from about six to thirty carbon atoms per molecule. Preferably, they have fourteen to thirty carbon atoms per molecule. Most preferably, they are predominately alpha olefins having from twenty to twenty-eight carbon atoms per molecule because these longer chain olefins impart desired oil solubility to the LOB and HOB sulfonates prepared from the corresponding alkylates. In this most preferred embodiment, small amounts of $C_{18}$ and $C_{30}$ olefins can be present.

ISOMERIZATION CATALYST

At least two types of acidic catalysts can be used for isomerization. The acidic catalyst can be solid or liquid.

Preferably, the first acidic catalyst is a solid catalyst having at least one metal oxide, and has an average pore size of less than 5.5 angstroms. More preferably, it is a molecular sieve with a one-dimensional pore system, such as SM-3, MAPO-11, SAPO-11, SSZ-32, ZSM-23, MAPO-39, SAPO-39, ZSM-22, and SSZ-20. Other possible solid, acidic catalysts useful for isomerization include ZSM-35, SUZ4, NU-23, NU-87, and natural or synthetic ferrierites. These molecular sieves are well-known in the art and are discussed in Rosemarie Szostak's *Handbook of Molecular Sieves* (New York, Van Nostrand Reinhold, 1992), and in U.S. Pat. No. 5,282,858, which is hereby incorporated by reference for all purposes.

Another type of isomerization catalyst that can be used is iron pentacarbonyl [$Fe(CO)_5$].

ISOMERIZATION PROCESS CONDITIONS

The isomerization process may be carried out in batch or continuous mode. The process temperatures can range from 50° C. to 250° C. In the batch mode, a typical method is to use a stirred autoclave or glass flask, which may be heated to the desired reaction temperature. A continuous process is most efficiently carried out in a fixed bed process. Space rates in a fixed bed process can range from 0.1 to 10 or more WHSV.

In a fixed bed process, the catalyst is charged to the reactor and activated or dried at a temperature of at least 150° C. under vacuum or flowing inert, dry gas. After activation, the catalyst is cooled to the desired reaction temperature and a flow of the olefin is introduced. The reactor effluent containing the partially branched, isomerized olefin is collected. The resulting partially-branched, isomerized olefin contains a different olefin distribution (alpha-olefin, beta-olefin; internal-olefin, trisubstituted-olefin and vinylidene-olefin) and branching content than the un-isomerized olefin.

ALKYLATION CATALYST

The second acidic catalyst is a solid catalyst that has at least one metal oxide, which is selected from the group consisting of natural zeolites, synthetic zeolites, synthetic molecular sieves, and clays. Preferably, the second solid, acidic catalyst comprises the acid forms of an acidic clay, or an acidic molecular sieve or a zeolite having an average pore size of at least 6.0 angstroms. Such zeolites include zeolite Y, beta, SSZ-25, SSZ-26, and SSZ-33. Other possible catalysts include L zeolite, mordenite, boggsite, cloverite, VPI-5, MCM-41, MCM-36, SAPO-8, SAPO-5, MAPO-36, SAPO40, SAPO-41, MAPSO-46, CoAPO-50, hexagonal faujasite (EMC-2), gmelinite, mazzite (omega zeolite), offretite, ZSM-18, and ZSM-12. These catalysts are discussed in Rosemarie *Szostak's Handbook of Molecular Sieves* (New York, Van Nostrand Reinhold, 1992).

More preferably, the second solid, acidic catalyst comprises zeolite Y. A preferred zeolite Y has a silica to alumina ratio of at least 40:1.

Useful acidic clays may be derived from naturally occurring or synthetic materials. One skilled in the art would realize that there are a number of such clays that are known to be alkylation catalysts. Examples of such acidic clays include montmorillonite, laponite, and saponite. Pillared clays may also be used as catalysts.

ALKYLATION PROCESS CONDITIONS

The alkylation reaction is typically carried out with an aromatic and an olefin in molar ratios from 1:15 to 25:1. Process temperatures can range from 100° C. to 250° C. As the olefins have a high boiling point, the process is preferably carried out in the liquid phase. The alkylation process may be carried out in batch or continuous mode. In the batch mode, a typical method is to use a stirred autoclave or glass flask, which may be heated to the desired reaction temperature. A continuous process is most efficiently carried out in a fixed bed process. Space rates in a fixed bed process can range from 0.01 to 10 or more WHSV.

In a fixed bed process, the catalyst is charged to the reactor and activated or dried at a temperature of at least 150° C. under vacuum or flowing inert, dry gas. After activation, the catalyst is cooled to ambient temperature and a flow of the aromatic compound is introduced. Pressure is increased by means of a back pressure valve so that the pressure is above the bubble point pressure of the feed composition at the desired reaction temperature. After pressurizing the system to the desired pressure, the temperature is increased to the desired reaction temperature. Optionally, the toluene may be added to the catalyst at reaction temperature. A flow of the olefin is then mixed with the toluene and allowed to flow over the catalyst. The reactor effluent containing alkylate product and excess aromatic is collected. Excess aromatic is then removed by distillation, stripping, evaporation under vacuum, or other means known to those skilled in the art.

ALKYLATION PRODUCT

This process produces alkylated aromatic hydrocarbons having the following properties:

(a) less than 40 wt. % of the alkylated aromatic hydrocarbon is characterized by having 2-aryl attachment;

(b) at least 20 wt. % of the alkylated aromatic hydrocarbon is a monoalkylate; and (c) no more than 90% of the alkyl groups are branched.

Preferably, at least 75 wt. % of the alkylated aromatic hydrocarbon is a monoalkylate.

For practical purposes, we have found that the "branching content" for aromatics alkylated with solid catalysts is determined by the degree of the isomerization introduced into the olefin feed during the olefin pre-isomerization step. We have confirmed that the subsequent alkylation step does not alter this "branching content" and hence the branching contents described herein are those pertaining to the olefin feed rather than the alkylate itself.

EXAMPLES

The invention will be further illustrated by following examples, which set forth particularly advantageous method embodiments. While the Examples are provided to illustrate the present invention, they are not intended to limit it.

Example 1

TOLUENE ALKYLATION WITH A ZEOLITE Y POWDER

A commercial acidic zeolite Y powder, with $SiO_2/Al_2O_3=$ 59, was calcined at 595° C. in air. The powder was pelletized and then crushed and sieved to produce catalyst particles with a size from 20 to 40 mesh. The zeolite particles were charged to a ½" OD fixed bed reactor with inert alundum packing above and below the catalyst. The catalyst bed was positioned to be in the isothermal zone of a single zone furnace. The catalyst was activated by flowing over it dry nitrogen gas (100 SCCM) and heating at 200° C. for six hours. It was then cooled to ambient temperature. Toluene (dried to 30 ppm by weight of water) was then allowed to flow over the catalyst at 2.0 cc/hr. After the catalyst was saturated with toluene, the pressure was increased to 175 psig by means of a back pressure regulator. When the system came to pressure, the catalyst was heated by means of the furnace to 170° C. When both temperature and pressure equilibrium was reached, the toluene flow over the catalyst was replaced with a mixture of toluene and $C_{20-24}$ olefin in an 8:1 molar ratio. The olefin was pre-isomerized $C_{20-24}$ NAO having the following composition: less than 1.0% alpha-olefin, 22% beta-olefin, 98% internal-olefin, 2.3% tri-substituted olefin, 0.1% vinylidene-olefin by Carbon NMR and 11% branching by IR. The feed rate was 2.04 cc/hr, giving a 1.03 WHSV. Samples of the reactor effluent were collected periodically for analysis by gas chromatography and supercritical fluid chromatography. The rest of the effluent was saved in several large fractions. At 333 hours the temperature was raised to 190° C. Over the first 355 hours the olefin conversion was essentially 100%. At 361 hours the temperature was increased to 210° C. At this temperature olefin conversion remained at about 100% but cracking reduced the yield of the alkylate product slightly. At 383 hours the feed rate was increased to 2.73 cc/hr, giving 1.37 WHSV. At 407 hours, temperature was decreased to 200° C., reducing the amount of cracking. At 482 hours, the feed rate was increased to 3.08 cc/hr, giving a 1.55 WHSV. At 492 hours the feed rate was increased to 3.41 cc/hr or a 1.72 WHSV. At 551 hours the temperature was reduced to 190° C., which eliminated cracking and restored the high yield of alkylate. At 553 hours a new feed with 10:1 molar ratio of toluene to olefin was started at a flow rate of 4.00 cc/hr or 2.02 WHSV. The run was terminated at 691 hours, at which time the olefin conversion was still about 100%.

Example 2.

TOLUENE ALKYLATION WITH A Y82-TYPE ZEOLITE POWDER

Toluene alkylation was done as described in Example 1, except that a Y82-type zeolite powder was used. The zeolite Y had a $SiO_2/Al_2O_3$ ratio of about 5.8. The catalyst (1.82 grams pelletized, crushed, and sieved to a size range of 20 to 40 mesh) was charged to a ½" OD reactor. After activation for 6 hours at 200° C., the catalyst was contacted with flowing toluene and equilibrated at 170° C. and 175 psig. A mixture of toluene and olefin (using the olefin described in Example 1) in an 8:1 molar ratio was allowed to contact the catalyst at 3.20 cc/hour giving a 1.48 WHSV. Complete conversion of olefin was observed for 370 run hours. At this point olefin breakthrough occurred and the run was terminated.

Example 3

TOLUENE ALKYLATION WITH A ZEOLITE Y EXTRUDATE

A zeolite Y catalyst extrudate was made using the zeolite Y powder described in Example 1. This catalyst consisted of 80% by weight zeolite and 20% by weight alumina. It was made by mixing the zeolite Y powder with acid-peptized alumina and extruding, using methods known to those skilled in the art. The resulting extrudates were ¹⁄₂₀" in diameter. The extrudates were calcined. A portion of the calcined extrudates was crushed and sieved to obtain particles with a size between 20 and 40 mesh.

The 20/40 mesh catalyst (2.22 grams) was charged to a ½" OD reactor and activated as described in Example 1. The alkylation test was conducted in the same manner as described in Example 1. After equilibrating at 180° C. and 175 psig with toluene, a mixture of toluene and olefin (using the olefin described in Example 1) in a 10:1 molar ratio was allowed to contact the catalyst at 1.45 cc/hour, giving a WHSV of 0.55. For the next 456 run hours, olefin conversion was essentially 100%. At this time, the feed rate was increased to 2.17 cc/hr or 0.82 WHSV. At 481 run hours the feed rate was increased to 3.41 cc/hr or 1.30 WHSV. Complete conversion of olefin was observed until 730 run hours. At that time olefin breakthrough occurred and the run was terminated.

Example 4

TOLUENE ALKYLATION WITH ENGELHARD F24 ACIDIC CLAY CATALYST

Toluene alkylation with a commercial F24 acidic clay catalyst was carried out in a manner similar to Example 1. The F24 catalyst (1.82 grams, crushed and sieved to 20/40 mesh) was charged to a reactor and activated for six hours at 200° C. under nitrogen flow. A flow of 1.09 cc/hr of a mixture of toluene and olefin in a 10:1 molar ratio (using the olefin described in Example 1) was started at ambient temperature. After the catalyst was saturated, pressure was increased to 175 psig. Upon equilibration of pressure, the temperature was increased to 170° C. Start of run was the time that heating was begun. Olefin conversion was 99% at 46 run hours and essentially 100% at 120 hours. Olefin breakthrough occurred at 230 hours and the run was terminated.

Example 5

TOLUENE ALKYLATION WITH SÜD-CHEMIE TONSIL ACIDIC CLAY CATALYST

Toluene alkylation with an acidic clay catalyst from Süd-Chemie AG was carried out as described in Example 1. The granulated material (3.24 grams) was charged to the reactor and activated at 200° C. under nitrogen. After equilibration with toluene at 200° C. and 175 psig, a flow was begun of 2.51 cc/hr (0.65 WHSV) of a mixture of toluene and olefin in a 10:1 molar ratio (using the olefin described in Example 1). At 23 run hours the temperature was decreased to 190° C. and the feed rate was decreased to 1.68 cc/hr (0.44 WHSV). Initial olefin conversion was about 99% and increased to essentially 100% during the first 200 hours. Olefin breakthrough occurred at about 370 hours and the run was terminated.

| Product | % Olefin Conversion | % 2-tolyl Content | % Heavy Alkylate | % Branched Alkylate |
|---|---|---|---|---|
| Example 1 | 99.6 | 15.3 | 2.8 | 3.0 |
| Example 2 | 99.2 | 12.7 | ~0 | 2.0 |
| Example 3 | 99.6 | 13.4 | 0.3 | 16.2 |
| Example 4 | 98.7 | 16.0 | 3.5 | 18.1 |
| Example 5 | 99.1 | 15.1 | 2.7 | 18.4 |

Example 6

PRE-ISOMERIZATION OF $C_{20-24}$ NAO USING IRON PENTACARBONYL (FE(CO)$_5$) IN A BATCH REACTION

Approximately 16 liters of $C_{20-24}$ NAO (dried by azeotropic distillation with toluene under nitrogen, and stripped of toluene at 400 mm Hg) in a 25 liter three-neck round bottomed flask fitted with a mechanical stirrer, thermowell for a temperature controller thermocouple, and a reflux condenser, was sparged with dry nitrogen gas for four hours at approximately 45° C. Under positive nitrogen pressure, approximately 10 cc of iron pentacarbonyl was added in one portion to the olefin with stirring. The temperature was raised to 190° C. and held at this temperature for approximately five hours. The reaction was then cooled to room temperature with stirring under nitrogen and then 350 grams of silica gel were added in portions with stirring, followed by approximately 7 cc of methanesulfonic acid. This mixture was heated to 175° C. over thirty minutes and held at this temperature for approximately three hours and then cooled to 25° C. The isomerized olefin was filtered through a Buchner funnel containing a one inch pad of filter aid with the aid of vacuum. The isomerized olefin was then washed with 400 cc portions of distilled water until the washings were neutral, and then it was washed twice more. The isomerized olefin product was then azeotropically dried with toluene using a Dean Stark Trap. When no more water was collected in the trap, the toluene was distilled from the olefin under approximately 350 mm Hg of vacuum. The final product was filtered several more times through filter aids to reduce the orange color. The final product contained 11 ppm Fe (by AAS) and had the following composition: 0.8% alpha-olefin, 15.0% beta-olefin, 99.2% internal-olefin, 0.2% tri-substituted olefin, 9.5% vinylidene-olefin by Carbon NMR, and 11% branching by IR.

Example 7

PRE-ISOMERIZATION OF A $C_{20-24}$ NORMAL ALPHA OLEFIN—FLOW REACTOR $C_{20-24}$ Normal Alpha Olefin with the following composition: alpha-olefin 89.1%, beta-olefin 0.5%, internal-olefin 1.4%, tri-substituted olefin 0.2%, vinylidene-olefin by Carbon NMR 9.5%, and branching by IR 11%, was pumped up-flow through a fixed bed reactor (570 mm high×22.3 mm ID) containing 65 grams of solid olefin isomerization catalyst (SAPO-11) operating isothermally at 160° C. at a LHSV of 0.5 hr$^{-1}$ and at atmospheric pressure. Four samples were collected having the following composition:

| Sample Number | 1 | 2 | 3 | 4 |
|---|---|---|---|---|
| Amount (liters) | 0.2 | 1.1 | 1.1 | 3.4 |
| % Alpha-Olefin | 5.7 | 5.6 | 1.8 | 3.8 |
| % Beta-Olefin | 33.8 | 28.0 | 33.6 | 35.4 |
| % Internal-Olefin | 88.0 | 85.0 | 96.0 | 92.0 |
| % Tri-Substituted-Olefin | 5.8 | 9.4 | 2.5 | 4.2 |
| % Vinylidene-Olefin | 0 | 0.2 | 0.3 | 0 |
| % Branching | 23 | 24 | 24 | 24 |

These samples were combined to afford a sample with the following weight averaged composition: 3.7% alpha-olefin, 33.6% beta-olefin, 91.3% internal-olefin, 5.0% tri-substituted-olefin, 0% vinylidene olefin, and 24% branching.

PROCEDURE FOR DETERMINING OLEFIN DISTRIBUTION OF PRE-ISOMERIZED NORMAL ALPHA OLEFINS BY CARBON NUCLEAR MAGNETIC RESONANCE (NMR)

A Varian Gemini NMR spectrometer operating at 300 MHz was used to determine the olefin distribution in the pre-isomerized normal alpha olefins. A macro was written to calculate the relative percent of alpha, beta, internal, tri-substituted, and vinylidene olefins present from the integration of the $^{13}$C NMR spectra (recorded in CDCl$_3$ containing a relaxation agent, Chromium (III) acetylacetonate, with a sufficient pulse delay to make the integrals more quantitative). The vinylidene olefin content was indicated as the sum of the C$_2$ and C$_4$ and higher vinylidene olefins present. The spectral regions used to determine the various olefin species present were as follows:

| Integral Olefin Species | Description | Chemical Shift (ppm) | Code |
|---|---|---|---|
| Alpha-Olefins | C1 | 113.0–115.4 | C |
|  | C2 | 137.6–140.0 | I |
| Beta-Olefins | C2 Z/E | 122.5–126.0 | E |
|  | C3 Z/E | 130.9–132.5 | G |
| Internal-Olefins | RHC=CHR Z/E | 129.0–130.8 | F |
| Tri-Substituted-Olefins | =CRH | 117.0–119.5 | D |
|  | =CRR' | 134.0–137.5 | H |
| Vinylidene-Olefins | =CH$_2$ | 106.7–108.0 | A |
|  |  | 108.1–109.6 | B |
|  | =CRR' Z/E | 149.0–150.5 | J |
|  |  | 150.6–152.0 | K |
| Total | — | — | Total A–K |

The percent of each olefinic species present is calculated from the integral of each region (Integral Code) above as follows:

% Alpha-Olefin=((C+I)/Total)×100

% Beta-Olefin=((2×G)/Total)×100

% Internal-Olefin=(((2×G)+F)/Total)×100

% Tri-Substituted-Olefin=((D+E+H−G)/Total)×100

% Vinylidene-Olefin=((A+K+B+J)/Total)×100

PROCEDURE FOR DETERMINING BRANCHING OF PRE-ISOMERIZED NORMAL ALPHA OLEFINS BY INFRARED SPECTROMETRY (IR)

The procedure is based on using the absorbance at 1378 cm$^{-1}$ for the C—CH$_3$ symmetric deformation as a measure of branching using reference standards. The reference standards were prepared from samples of isomerized C$_{20-24}$ NAO that had been hydrogenated and analyzed by Gas Liquid Phase Chromatorgraphy (GLPC) to determine the branching content. A calibration curve was constructed by plotting the percent branching of the reference standards determined by GLPC versus the absorbance at 1378 cm$^{-1}$ observed by IR. The procedure for determining the absorbance at 1378 cm$^{-1}$ consisted of dissolving 50 weight % of an isomerized olefin into chloroform (Spectral Grade) and placing the sample in a liquid IR cell of given path length. A background spectrum was obtained using a blank (N$_2$). The absorption spectrum between 1200 cm$^{-1}$ and 1600 cm$^{-1}$ was obtained. The region between 1200 cm$^{-1}$ and 1400 cm$^{-1}$ was expanded and a base line drawn between the valleys that occur at approximately 1395 cm$^{-1}$ and 1325 cm$^{-1}$. Then the absorbance from the baseline to the top of the peak at 1378 cm$^{-1}$ was measured. The percent branching was then determined from the calibration curve generated with the reference standards.

PROCEDURE FOR DETERMINING MONO ALKYLATE 2-TOLYL CONTENT OF C$_{20-24}$ ALKYL TOLUENE ALKYLATES BY GAS LIQUID PHASE CHROMATOGRAPHY (GLPC)

A Hewlet Package 5880 Gas Chromatograph fitted with a 50 meter×0.2 mm×0.5 micron PONA (cross-linked methyl silicone gum) capillary column was used operating with a FID detector at 300° C. and an injector temperature of 300° C. The oven temperature profile used was as follows:

Initial Temp 100° C.

Ramp to 150° C. at 30° C./min

Ramp to 250° C. at 15° C./min

Ramp to 290° C. at 5° C./min

Hold at 290° C. for 75 minutes

In general, the last three peaks that elute from the column for each carbon number alkylate species (i.e. the C$_{20}$ alkylates, the C$_{22}$ alkylates, and the C$_{24}$ alkylates) were the alkyl toluene species in which the alkyl chain was attached at the 2-position along the alkyl chain. The three peaks for each carbon number were the ortho, meta, and para-alkyl isomers. For the C$_{20-24}$ toluene alkylate under the conditions that contribute to the relative retention times (carrier gas flow, condition of the column, and other factors), these peaks were in the following regions:

| Alkyl Toluene | 2-Tolyl Species Retention Time Region (minutes) |
|---|---|
| C$_{20}$ | 41.5–43.3 |
| C$_{22}$ | 54.5–57.2 |
| C$_{24}$ | 74.0–78.0 |

The percent Mono-Alkylate 2-Tolyl Content was calculated by the following equation:

$$\frac{\text{Mono-Alkylate}}{\text{2-Tolyl Content}} = \frac{\text{Area of Peaks for 2-Tolyl Species}}{\text{Area of All Peaks for Mono-Alkylate Species}}$$

(Between 28 and 78 minutes)

PROCEDURE FOR DETERMINING CONVERSION AND "HEAVIES" CONTENT OF C$_{20-24}$ ALKYL TOLUENE ALKYLATES BY SUPERCRITICAL FLUID CHROMATOGRAPHY (SFC)

A Dionex, Lee Scientific Model 600 Supercritical Fluid Chromatograph (SFC) equipped with a 10 meter×195 micron OD/50 micron ID, 0.25 micron film SB-Methyl-100 capillary column, an FID detector operating at 325° C., and carbon dioxide eluent, was used with split injection. The following density ramp program was used (isothermal oven at 100° C.):

Initial Density=0.2 g/cc

Inject Sample

Hold five minutes

Ramp to 0.3 g/cc at 0.02 g/cc/min

Ramp to 0.5 g/cc at 0.01 g/cc/min

Ramp to 0.76 g/cc at 0.02 g/cc/min

Hold 12 minutes

For the C$_{20-24}$ toluene alkylate under the conditions that contribute to the relative retention times (carrier gas flow, condition of the column, and other factors), the C$_{20-24}$ unreacted olefins eluted between 22 and 27.5 minutes. The C$_{20-24}$ toluene mono-alkylate eluted between 28 and 36 minutes, and the "Heavies" eluted between 37 and 45 minutes.

The purity of the alkylate and percent "heavies" was calculated as follows:

$$\frac{\text{Percent Alklate}}{\text{Purify}} = \frac{\text{Peak Area between 28 and 45 minutes}}{\text{Peak Area between 22 and 45 minutes}} \times 100$$

$$\text{Percent "Heavies"} = \frac{\text{Peak Area between 37 and 45 minutes}}{\text{Peak Area between 28 and 45 minutes}} \times 100$$

Example 8

BATCH PREPARATION OF A $C_{20-24}$ NAO TOLUENE ALKYLATE WITH 19% 2-TOLYL, 24% HEAVIES, AND 24% BRANCHING CONTENT

To a 25 liter three-neck round bottom flask equipped with a mechanical stirrer, a Dean Stark Trap fitted with a water cooled condenser and a thermowell for the temperature controller thermocouple was added 3884 grams of toluene followed by 3245 grams (approximately 10.54 moles) of a mixture of pre-isomerized $C_{20-24}$ NAO having the following composition (4% alpha-olefin, 34% betaolefin, 91% internal-olefin, 5% tri-substituted olefin, 0% vinylidene-olefin by Carbon NMR, and approximately 24% branching by IR) from Example 7. To this solution was added 3440 grams of AMBERLYST® 36 (a solid acidic sulfonic acid resin catalyst commercially available from Rohm & Haas, Philadelphia, Pa., USA that had been dried azeotropically using refluxing toluene) in one portion with stirring. The reaction was placed under a positive pressure of dry nitrogen connected to a bubbler. The reaction temperature was increased to 113° C. and the progress of the reaction was monitored by analyzing by supercritical fluid chromatography (SFC) reaction aliquots withdrawn from the reaction at various times. After approximately 66 hours, SFC analysis showed 99.3% conversion of the olefin. The reaction was cooled to room temperature and filtered through a sintered glass Buchner funnel (coarse porosity) with the aid of vacuum to remove the catalyst. The resulting organic fraction was distilled to remove the toluene (82° C./660 mm Hg) to give the final product: 99.2% pure alkylate containing 24.1% "Heavies" by SFC and 19% 2-tolyl mono-alkylate content by GLPC.

Example 9

BATCH PREPARATION OF A $C_{20-24}$ NAO TOLUENE ALKYLATE WITH 20% 2-TOLYL, 17% HEAVIES, AND 11% BRANCHING CONTENT

The procedure used to prepare the product in Example 8 was followed exactly except the pre-isomerized $C_{20-24}$ NAO used had the following composition: less than 1% alpha-olefin, 22% beta-olefin, 98% internal-lefin; 2.3% tri-substituted olefin, 0.1% vinylidene-olefin by Carbon NMR, and 11% branching by IR. After approximately 23 hours, the SFC showed 99.5% conversion of the olefin. The final product showed: 99.9% pure alkylate containing 17.0% "Heavies" by SFC and 20.2% mono-alkylate 2-tolyl content by GLPC.

Example 10

BATCH PREPARATION OF A $C_{20-24}$ NAO TOLUENE ALKYLATE WITH 10% 2-TOLYL, 2% HEAVIES, AND 11% BRANCHING CONTENT

A 5 liter three-neck round bottom flask was equipped with a mechanical stirrer, a Dean Stark Trap fitted with a water cooled condenser and a thermowell for the temperature controller thermocouple. To this flask was added a dry Type 4A Molecular Sieve, a mixture of 1368 grams of toluene and 1144 grams of a mixture of pre-isomerized $C_{20-24}$ NAO obtained from Example 6, having the following composition: less than 1.0% alpha-olefin, 22% beta-olefin, 98% internal-olefin, 2.3% tri-substituted olefin, 0.1% vinylidene-olefin by Carbon NMR, and 11% branching by IR. (The Type 4A Molecular Sieve was dried overnight at 100° C./17 hours in air.) To this solution was added 656 grams of zeolite Y (1.8 mm extrudate) that had been activated at 100° C. for 17 hours (calcined at 535° C. for ten hours in air). The reaction was placed under a positive pressure of dry nitrogen connected to a bubbler. The reaction temperature was increased to 113° C. and the progress of the reaction was monitored by supercritical fluid chromatography (SFC) by analyzing reaction aliquots withdrawn from the reaction at various times. After approximately 30 hours, SFC analysis showed 99.5% conversion of the olefin. The reaction was cooled to room temperature and filtered through a sintered glass Buchner funnel (coarse porosity) containing a filter aid with the aid of vacuum to remove the catalyst. The resulting organic fraction was distilled to remove the toluene (82° C./660 mm Hg) to give the final product: 99.6% pure alkylate containing 1.9% "Heavies" by SFC, and 9.5% mono-alkylate 2-tolyl content by GLPC.

Example 11

BATCH PREPARATION OF A $C_{20-24}$ NAO TOLUENE ALKYLATE WITH 10% 2-TOLYL, 0% HEAVIES, AND 90% BRANCHING CONTENT

To a 30 cc glass serum bottle was added 1.0 grams of zeolite Y (1.8 mm extrudate calcined at 535° C. for ten hours in air). The bottle was then placed in an oven at 100° C. in air for approximately 17 hours. The bottle was then removed from the oven and immediately sealed with a TEFLON® rubber faced septum using a crimpon tool. After the bottle had cooled to room temperature, 20 cc of a mixture of 9.1 grams of toluene and 7.6 grams (0.025 moles) of a mixture of pre-isomerized $C_{20-24}$ NAO having the following composition (18.7% alpha-olefin, 27.1% beta-olefin, 40.3% internal-lefin, 41.6% tri-substituted olefin, 0% vinyl idene by Carbon NMR, and approximately 90% branching by IR) that had been pre-dried about 14 hours over activated (150° C. for 12 hours) Type 4A Molecular Sieve via syringe. The bottle was then placed in a oil bath maintained at between 145° C. and 155° C. After 24 hours, the bottle was removed and allowed to cool to room temperature and then the bottle was opened and the contents gravity filtered through filter paper. Analysis of the reaction mixture showed it to contain 99.3% pure alkylate containing 0% Heavies by SFC and 10.1% mono-alkylate 2-tolyl content by GLPC.

Example 12

BATCH PREPARATION OF A $C_{20-24}$ NAO TOLUENE ALKYLATE WITH 10% 2-TOLYL, 0% HEAVIES, AND 70% BRANCHING CONTENT

The procedure used in Example 11 was followed exactly except the pre-isomerized $C_{20-24}$ NAO used had the following composition: 7.2% alpha-olefin, 22% beta-olefin, 43.2% internal-olefin, 47.5% tri-substituted olefin, 2.1% vinylidene-olefin by Carbon NMR, and approximately 70% branching content by IR. The analysis of the reaction mixture after 24 hours showed a 99.3% pure alkylate containing 0% "Heavies" content and 10.2% mono-alkylate 2-tolyl content.

Example 13

BATCH PREPARATION OF A $C_{20-24}$ NAO TOLUENE ALKYLATE WITH 19% 2-TOLYL, 1% HEAVIES, AND 28% BRANCHING CONTENT

The procedure used in Example 10 was followed exactly except the pre-isomerized $C_{20-24}$ NAO used had the following composition: 25.4% alpha-olefin, 36.8% beta-olefin, 68.4% internal-olefin, 5.9% tri-substituted olefin, 0.3% vinylidene-olefin by Carbon NMR, and approximately 28% branching by IR. After approximately 31 hours of reaction time, SFC analysis showed 99.7% conversion of the olefin. The final product was found to be:

99.9% pure alkylate containing 1.0% "Heavies" by SFC and 19.2% $C_{20}$ 2-tolyl mono-alkylate content by GLPC.

Example 14

BATCH PREPARATION OF A $C_{20-24}$ NAO TOLUENE ALKYLATE WITH 12% 2-TOLYL, 7% HEAVIES, AND 24% BRANCHING CONTENT

The procedure in Example 10 was followed exactly except the pre-isomerized $C_{20-24}$ NAO used had the following composition: 3.1% alpha-olefin, 32.3% beta-olefin, 90.8% internal-olefin, 5.8% tri-substituted olefin, 0.3% vinylidene-olefin by Carbon NMR, and approximately 24% branching by IR). After approximately 40 hours of reaction time, SFC analysis showed 99.2% conversion of the olefin. The final product was found to be: 99.3% pure alkylate containing 6.9% "Heavies" by SFC and 11.6% mono-alkylate 2-tolyl content by GLPC.

Example 15

BRANCHING CONTENT IN THE ALKYL TOLUENE ALKYLATES

The percent branching content in the alkyl toluenes produced in Examples 8, 12, and 13 were determined following the procedure used to determine the branching content in olefins. The branching content of the alkyl toluenes and the corresponding pre-isomerized olefins are compared below.

| | Percent Branching Content | | |
|---|---|---|---|
| Sample | Alkyl Toluene (AT) | Corresponding Pre-Isomerized Olefin (CPIO) | Percent Difference (CPIO-AT) |
| Example 8 | 18.5 | 20.7 | 2.2 |
| Example 12 | 65.4 | 68.0 | 2.6 |
| Example 13 | 26.1 | 28.4 | 2.3 |

This example shows that the branching content in the alkyl toluene alkylates is simple dilution of the branching content in the corresponding pre-isomerized olefin.

Example 16

BATCH PREPARATION OF A $C_{20-24}$ NAO BENZENE ALKYLATE WITH 17% 2-PHENYL, 0% HEAVIES, AND 11% BRANCHING CONTENT

The procedure used in Example 11 was followed exactly except five cc of feed was used and the feed consisted of a mixture of the pre-isomerized $C_{20-24}$ NAO pre-mixed with benzene in a 4:1 molar ratio of benzene:olefin. In addition, the reaction was stirred in the vial by means of a magnetic stir bar. The analysis of the reaction mixture after 24 hours showed a 99.6% pure alkylbenzene alkylate containing 0% "Heavies" by SFC and 17.4% mono-alkylate 2-phenyl content by GLPC.

Comparison of the results of Examples 1 to 5 and Examples 10 to 14 show that alkylate products with comparable properties can be made with the same catalysts in either batch or continuous flow fixed bed experiments. It is known to those skilled in the art that process parameters such as pressure, temperature, residence time, space velocity, reactor and vessel configuration can affect the conversion and selectivities in the alkylation process. The conditions indicated herein are intended to be illustrative only and are not limiting.

While the present invention has been described with reference to specific embodiments, this application is intended to cover those various changes and substitutions that may be made by those skilled in the art without departing from the spirit and scope of the appended claims.

What is claimed is:

1. A process for producing an alkylated, non-oxygen-containing aromatic hydrocarbon, said process comprising:

(a) isomerizing a normal alpha-olefin in the presence of a first acidic catalyst to produce an isomerized olefin, wherein at least 11 weight % of the isomerized olefin is branched; and (b) alkylating a non-oxygen-containing aromatic hydrocarbon with said isomerized olefin in the presence of a second acidic catalyst, wherein the second acidic catalyst is a solid catalyst having at least one metal oxide, and wherein said second acidic catalyst is selected from the group consisting of natural zeolites, synthetic zeolites, synthetic molecular sieves, and clays.

2. A process according to claim 1 wherein the normal alpha-olefin has from 14 to 30 carbon atoms.

3. A process according to claim 1 wherein the first acidic catalyst is a solid catalyst comprising at least one metal oxide, and having an average pore size of less than 5.5 angstroms.

4. A process according to claim 3 wherein the first solid, acidic catalyst comprises a molecular sieve with a one-dimensional pore system.

5. A process according to claim 1 wherein the non-oxygen-containing aromatic hydrocarbon is selected from the group consisting of benzene, toluene, xylene, cumene, and mixtures thereof.

6. A process according to claim 1 wherein the second solid, acidic catalyst comprises either an acidic molecular sieve having an average pore size of at least 6.0 angstroms or a zeolite having an average pore size of at least 6.0 angstroms.

7. A process for producing an alkylated, non-oxygen-containing aromatic hydrocarbon, said process comprising:

(a) isomerizing a normal alpha-olefin having from 20 to 28 carbon atoms in the presence of a first acidic catalyst to produce a partially-branched, isomerized olefin; and (b) alkylating an aromatic hydrocarbon, selected from the group consisting of benzene and toluene, with said partially-branched, isomerized olefin in the presence of a second solid, acidic catalyst comprising zeolite Y.

8. A process according to claim 7 wherein the zeolite Y has a silica to alumina ratio of at least 40:1.

9. An alkylated aromatic hydrocarbon produced by the process according to claim 7, wherein said alkylated aromatic hydrocarbon has the following properties:

(a) less than 40 wt. % of the alkylated aromatic hydrocarbon is 2-aryl; and (b) at least 20 wt. % of the alkylated aromatic hydrocarbon is a monoalkylate.

10. An alkylated aromatic hydrocarbon produced by the process according to claim 9 wherein at least 75 wt. % of the alkylated aromatic hydrocarbon is a monoalkylate.

* * * * *